United States Patent [19]

Roncari

[11] 4,226,747

[45] Oct. 7, 1980

[54] IMMUNOLOGICAL DIAGNOSTIC REAGENTS COMPRISING THIO-AMINE TERMINATED LATEX PARTICLES

[75] Inventor: Gaetano Roncari, Ettingen, Switzerland

[73] Assignee: Hoffmann-La Roche Inc., Nutley, N.J.

[21] Appl. No.: 929,410

[22] Filed: Jul. 31, 1978

[30] Foreign Application Priority Data

Aug. 3, 1977 [CH] Switzerland .................. 9542/77

[51] Int. Cl.³ .............. A61K 39/00; C08L 25/00; C08L 89/00; G01N 31/00
[52] U.S. Cl. ........................................ 260/8; 260/6; 260/29.7 DP; 424/12; 424/79; 424/81; 435/180; 435/181; 435/182; 525/291
[58] Field of Search ............... 260/29.7 DP, 8, 6; 424/12, 81, 79

[56] References Cited

U.S. PATENT DOCUMENTS

| | | | |
|---|---|---|---|
| 3,857,931 | 1/1972 | Hager | 424/12 |
| 4,059,685 | 11/1977 | Johnson | 260/6 |
| 4,064,080 | 12/1977 | Daniel | 260/8 |
| 4,118,349 | 10/1978 | Bonacker et al. | 260/112 R |
| 4,134,872 | 1/1979 | Lee | 260/880 R |
| 4,140,662 | 2/1979 | Reckel et al. | 260/112 R |
| 4,156,669 | 5/1979 | Lee | 260/880 R |

FOREIGN PATENT DOCUMENTS

| | | | |
|---|---|---|---|
| 845402 | 8/1976 | Belgium | 260/8 |
| 1806418 | 6/1969 | Fed. Rep. of Germany | 424/12 |
| 2204684 | 8/1972 | Fed. Rep. of Germany | 424/12 |
| 2331567 | 6/1977 | France | 424/12 |
| 2001996 | 2/1979 | United Kingdom | 260/8 |

OTHER PUBLICATIONS

Chem. Absts., vol. 87:64403n, Carrier with side chains for fixing organic compounds with a glucide residue, Quash.
Chem. Absts. vol. 71:79250d, Protein-containing reagents, Adams et al.
Chem. Absts. vol. 77:137144j, Detecting Antigens or Anti-bodies in a body fluid, Cleeland et al.

*Primary Examiner*—Edward M. Woodberry
*Attorney, Agent, or Firm*—Jon S. Saxe; Bernard S. Leon; William H. Epstein

[57] ABSTRACT

A reagent for an immunological determination comprising water insoluble latex particles being formed from vinyl polymerizates and having free terminal functional groups of the formula:

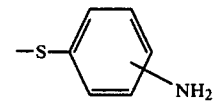

through which are bound an immunologically active material including materials for preparing this reagent and for utilizing this reagent for diagnostic purposes. The latex particles contain a core and an outer layer, said core being formed by polymerization of vinyl, or diene monomers or mixtures thereof with said polymerizates in said core carrying a functional group selected from group consisting of carboxyl, sulfonate or mixtures thereof and said outer layer being formed from vinyl polymerizates carrying said terminal functional group.

20 Claims, No Drawings

IMMUNOLOGICAL DIAGNOSTIC REAGENTS COMPRISING THIO-AMINE TERMINATED LATEX PARTICLES

BACKGROUND OF INVENTION

The diagnosis of pathological or other conditions in human beings and animals is often carried out using immunological principles. These principles are used for the detection of antibodies or antigens in the body fluids of the living beings. An antigen is a foreign substance which, when it is applied to the living being, brings about the formation of certain substances which are soluble and known as the antibody. Any substance such as, for example, a protein, which is normally not present in a specific living being, can cause the formation of antibodies when it is applied to the living being under suitable conditions.

After their formation, the antibodies react with the antigens and in this way protect against infections in the case of a bacteria or virus foreign body.

Immunological test processes depend on the antigen-antibody reaction, which usually manifests itself by insolubility or agglutination.

In general, the presence of an antigen or an antibody is confirmed or determined by adding the corresponding antibody or the corresponding antigen to a body fluid of the living being, mainly urine, blood serum or a specially treated blood extract. However, other body fluids can also be used. The presence or the absence of the antibody or the antigen in the body fluid of the living being is ascertained by establishing the occurrence or nonoccurrence of an antigen-antibody reaction.

Because some complexes only form very slowly and have very small particle sizes, it is necessary to use carriers in order to make them visible. In a hitherto preferred method the antibody or the antigen was bound by means of a carbodiimide via an amide bond to discrete particles of carboxylated latex polymers such as, for example, carboxylated copolymers of butadiene and sytrene.

This method has, however, the disadvantage that during the coupling of the protein (antibody or antigen) to the latex particles, there occurs as the side-reaction, because of the use of carbodiimides, an undesirable lattice-like polymerisation of the protein used and, accordingly, a part of the often very expensive protein is lost for the coupling with the carrier.

DESCRIPTION OF THE INVENTION

The present invention is concerned with polymeric carriers, with which the above disadvantages can be avoided and which can form with a wide spectrum of immunologically active materials a diagnostically useful reagent, which is stable, specific and sensitive and makes possible a readily detectable visual estimation in a very short time.

More particularly, the present invention is concerned with a water-insoluble reagent for an immunological determination having a specific weight corresponding to about that of water in the form of discrete latex particles, to which is bound an immunologically active material, wherein the latex consists of a dispersion of particles of vinyl polymerisates, which carry as the terminal functional groups, groups of the formula

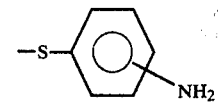

through which are bound an immunological reagent. The latex particles have a core formed from a vinyl and/or diene polymerisate carrying carboxyl and/or sulphonate functional groups, and an outer layer containing vinyl polymerisates, which carries as the terminal functional groups, groups of the formula

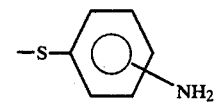

In accordance with this invention, the latex particles have an average diameter of from about 0.03 $\mu$m to about 5 $\mu$m.

Further, the present invention is concerned with a process for the manufacture of such a reagent, which process comprises reacting the latex, after diazotisation or in the presence of suitable bifunctional reagents, with the immunologically active material.

As "immunologically active substances" there can be named all constituents in physiological fluids, cell extracts and tissue extracts for which there is present or can be formed an immunological reaction partner. Thereto there belong amines, amino acids, peptides, proteins, lipoproteins, glycoproteins, sterols, steroids, lipoids, nucleic acids, enzymes, hormones, vitamins, polysaccharides and alkaloids. Preferred immunologically active substances are compiled in the Table I hereinater:

TABLE I

I. Antigens produced by microorganisms
   Bacteria
   1. Gram-positive cocci
      *Streptococci (pyogenes, fecalis* and *viridans)*
      *Staphylococci (aureus* and *albus)*
      *Pneumococci (D. pneumoniae)*
   2. Gram-negative cocci
      *Neisseria (gonorrhoeae* and *meningitidis)*
   3. Gram-positive, aerobic bacilli
      *Bacillus anthracis*
      *Corynebacterium diphtheriae*
      *Erysipelothrix*
      *Listeria monocytogenes*
   4. Gram-positive, anaerobic bacilli
      *Clostridia (botulinum, perfringens, welchii* and *tetani)*
   5. Gram-negative, anaerobic bacilli
      *Bacteroides*
   6. Gram-negative, intestinal bacilli
      *Escherichia*
      *Klebsiella*
      *Enterobacter*
      *Proteus*
      *Pseudomonas*
      *Salmonella*
      *Shigella*
   7. Gram-negative, non-intestinal bacilli
      *Pasteurella (pestis* and *tularensis)*
      *Hemophilus influenzae*
      *Brucella (melitensis, abortus* and *suis)*
      *Bordetella pertussis*
      *Malleomyces*
   8. Spirochetae
      *Treponema pallidum*
      *Leptospira*

TABLE I-continued

Borrelia
9. Mycoplasma
10. Mycobacteria
11. Vibrio
12. Actinomyces

Protozoa
1. Intestinal protozoa
   Amobae
2. Flagellates
   Trichomonas
   Leishmania
   Trypanosomes
   Toxoplasma (*T. Gondii*)
3. Sporozoa
   Plasmodia (*vivax, falciparum, malariae* and *ovale*)

Fungi
1. Sporotrichum
2. Crytococcus
3. Blastomyces
4. Histoplasma
5. Coccidioides
6. Candida Viruses and Rickettsia
1. Rickettsia
2. Viruses
   Canine hepatitis
   Shope papilloma
   Influenza A & B
   Fowl pest
   Herpes simplex
   Adenoviruses
   Polyoma
   Rous sarcoma
   Vaccinia
   Polio virus
   German measles
   Canine distemper
   Leukaemia
   Mumps
   Newcastle disease (domestic fowl disease)
   Sendai
   ECHO
   Foot and mouth disease
   Psittacosis
   Rabies
   Ectromelia
   Arborviren II. Foreign antigens
   Polysaccharides
   Hyaluronidases
   Tetanus toxin
   Egg ovalbumin
   Sheep serum albumin
   Human plasma gammaglobulin
   Human serum albumin III. Natural antigens
1. Hormones
   Insulin
   Glucagon
   Thyroid hormone
   Choriongonadotropin
   Chorion growth hormone - prolactin
2. Enzymes
   *Pancreas chymotrypsinogens*
   Procarboxypeptidases
   Deoxyribonucleases
   Ribonucleases
   Catalases
   *Creatin phosphokinases*
3. Organ-specific antigens
   Kidney
   Liver
   Skin
   Heart (myoglobin)
   Gastrointestinal tract
   Prostate
   Embryo antigens (e.g. CEA antigen)
   Tumour antigens
4. Connective tissue components
   Muscle

TABLE I-continued

Collagen
Amyloid
5. Blood cell antigens, blood group substances and other isoantigens
   Platelets
   Megacaryocytes
   Leucocytes
   Erythrocytes
   Blood group substances
   Forssman antigen
   Histo-compatible antigens
6. Plasma proteins
   Fibrin and fibrinoid
   Plasminogen and plasmin
7. Pathological globulins
   Myeloma, macroglobulinaemic and dysglobulinaemic proteins
   Rheumatoid factor
   C-reactive proteins IV. Natural antibodies
1. Natural gammaglobulins
   Natural antibodies - nephrotoxic antibody complement
2. Auto-antibodies
   Antinuclear factor
   Thyroid autoantibodies
   Adrenal autoantibodies
   Autoantibodies for gastric-parietal cells in the case of pernicious anaemia
   Autoantibodies for spermatozoa
   Muscle autoantibodies in the case of Myasthenia gravis
   Autoantibodies for nerve tissue
   Autoantibodies against fibre-like tissue and vascular components
   Autoantibodies against platelets and megacaryocytes
   Antibodies against trophoblasts
3. Induced antibodies against:
   Immunoglobulin classes IgG, IgA, IgM or variant species V. Haptenic compounds
   Opium alkaloids (morphine)
   Antipyrine
   Barbituric acid Especially preferred immunologically active substances in the scope of the present invention are albumin, rheumatoid factor, human immunoglobulin IgG and antibodies against IgG.

Under vinyl polymerisates, which form the core of the particles, there are to be understood homopolymerisates of monomers such as styrene and its derivatives: methylstyrenes, ethylstyrenes, vinyltoluene; vinyl chloride, vinylidene chloride; vinyl acetate; acryl derivatives such as allkyl acrylates and alkyl methacrylates (the alkyl groups containing 1 to 10 carbon atoms), which are optionally hydroxylated, such as 2-hydroxyethyl acrylate, 2-hydroxyethyl methacrylate, 2-hydroxypropyl acrylate and 2-hydroxypropyl methacrylate; and acrylonitrile and methacrylonitrile; as well as copolymerisates of these monomers with one another and/or with modified vinyl comonomers such as divinylbenzene, acrylamide and methacrylamide and their N-substituted derivatives such as, for example, methylolacrylamide; these comonomers represent up to 5 wt.% of the copolymerisate.

Under diene polymerisates, which form the core, there are to be understood homopolymerisates of butadiene and its derivatives: chloroprene, isoprene; as well as copolymerisates of these monomers with one another and/or with vinyl monomers, such as those mentioned earlier, in all ratios and/or with modified acting vinyl monomers, as mentioned earlier, whose amounts constitute up to 5 wt.% in the copolymerisate.

The vinyl polymerisates, which form the outer layer of the particle, are homopolymerisates of monomers such as styrene and its derivatives, e.g. methylsytrene, ethylstyrene and vinyltoluene; optionally hydroxylated alkyl acrylates and alkyl methacrylates (the alkyl groups containing 1 to 10 carbon atoms); acrylonitrile and methacrylonitrile; as well as copolymerisates of these monomers with another and/or with modified acting vinyl comonomers such as divinylbenzene, acrylamide and methacrylamide as well as their N-substituted derivatives such as methylolacrylamide, which can constitute up to 5 wt.% of the copolymerisate.

In the particles, the core polymerisate represents about 30 wt.% to about 99.5 wt. %, preferably from about 60 wt.% to about 99 wt. %, and the polymerisate of the outer layer represents from about 70 wt. % to about 0.5 wt.%, preferably from about 40 wt. % to aout 1 wt. %.

The polymerisate particles, whose particle distribution can be wide or narrow depending on the desired properties of the latex and on the intended use, have an average diameter between 0.03 µm and 5 µm, preferably between 0.05 µm and 1 µm. They represent up to about 60 wt. %, preferably up to about 45 wt. % of the latex. However, the latex can be diluted or concentrated.

The core polymerisate can be manufactured by emulsion polymerisation of the vinyl monomer(s) and/or diene monomer(s) in the presence of at least one ethylenic monocarboxylic acid or polycarboxylic acid which is copolymerisable with the monomer(s) and/or at least one copolymerisable unsaturated alkali organosulphonate. Then, the polymerisate of the outer layer is manufactured by emulsion polymerisation of the vinyl monomer(s) in the presence of the latex of the core polymerisate, manufactured as described earlier, and in the presence of a chain-propagating agent.

The monomers used in the polymerisation of the core polymerisate and in the polymerisation of the polymerisate of the outer layer are monomers which are mentioned earlier. They are either used all before the polymerisation or are used in part before the polymerisation, whereby the remaining part is added to the reaction medium in the course of the polymerisation in successive fractions or continuously, or all is added in the course of the polymerisation in successive fractions or continuously.

As copolymerisable ethylenic monocarboxylic acids or polycarboxylic acids there may be named acrylic acid methacrylic acid, maleic acid, fumaric acid, crotonic acid, sorbic acid, cinnamic acid, itaconic acid and aconitic acid, such acids being used in an amount of from about 0.5 wt. % to about 15 wt. %, preferably from about 0.5 wt. % to about 10 wt. %, based on the monomer(s).

The copolymerisable unsaturated alkali organosuphonates are, for example, sodium vinylsulphonate, sodium methallylsulphonate, sodium 2-sulphoethylacrylate, sodium 2-sulphoethylmetacrylate and 2 acrylamido-2-methylpropane-sulphonate. They are used in an amount from about 0.1 wt. % to about 3 wt. % based on the monomer(s).

The copolymerisable ethylenic monocarboxylic acids or polycarboxylic acids and the copolymerisable unsaturated alkali organosulphonates can be used individually or in combination in the given amounts.

The manufacture of the core polymerisate may be carried out in emulsion according to any conventional process well known in the art. Generally, it is preferred to carry out the polymerisation presence of an initiator and an emulsifier.

As the initiator there is preferably used an alkali persulphate, a water-soluble diazo derivative or a Redox system based on hydrogen peroxide, an organic peroxide or hydroperoxide in an amount in the order of from about 0.01 wt. % to about 5 wt. %, preferably from about 0.03 wt. % to about 3 wt. %, based on the monomer(s).

The emulsifier used can be anion-active and/or non-ionic. The emulsifier is a classical emulsifier used in emulsion polymerisation.

As anion-active emulsifiers there may be named salts of fatty acids; alkali alkylsulphates, alkali alkylsulphonates, alkali alkylarylsulphonate, alkali alkylsulphosuccinates, alkali alkylphosphates; sulphosuccinic acid alkyl ester; sulphonates of alkylphenol polyglycol ethers; salts of esters of alkylsulphopolycarboxylic acids; condensation products of fatty acids with oxyalkanesulphonic acids and aminoalkanesulphonic acids; sulphated derivatives of polyglycol ethers; sulphated esters of fatty acids and polyglycols; alkanolamides of sulphated fatty acids.

As non-ionic emulsifiers there can be mentioned fatty acid esters of polyalcohols, alkanolamides of fatty acids, polyethyleneoxides, copolyethyleneoxide/-propyleneoxide, oxyethylated alkylphenols.

The amount of emulsifier(s) which may be used lies in the range of from about 0.01 wt. % to about 5 wt. % based on the monomer(s) and its introduction may be carried out either all together before the polymerisation or in part before the polymerisation, whereby the remaining part may be added to the reaction medium in the course of the polymerisation in successive fractions or continuously, or all together in the course of the polymerisation in successive fractions or continuously.

The amount of water which may be used in the polymerisation of the core polymerisate must be such that the concentration of the monomer(s) does not exceed 60 wt. %.

Although it is not absolutely necessary, it is possible to add to the reaction medium compounds which are either capable of modifying the ionic strength of the medium and accordingly the particle distribution such as mineral acids or electrolytes in an amount up to 3 wt.% based on the monomers or which are capable of modifying the pH value of the medium such as, for example, buffers, acids or bases. However, it has been established in certain cases that for the promotion of the copolymerisation it is preferred for the medium to be neutral or acid.

The temperature at which the polymerisation is carried out is a function of the initiator used and of the polymerisate to be manufactured and generally ranges from about −5° C. to about +90° C.

The lattices obtained have polymerisate particles with a diameter of from about 0.03 µm to about 5 µm, preferably of from about 0.05 µm to about 1 µm. These particles are generally not calibrated, but it is possible to obtain them calibrated when the known calibration process is used for the emulsion polymerisation, such as the controlled addition of the emulsifier and/or of the monomer(s) and especially inoculation. In the latter case, the emulsifier can be contained in the inoculation material.

The particles are formed from homopolymerisates or copolymerisates having a surface of carboxyl and/or sulphonate functions. The existence of these functions can be confirmed by conductometric titration.

The manufacture of the polymerisate of the outer layer is carried out in aqueous emulsion in the presence of the core polymerisate, a chain-propagating agent, an initiator and, if desired, an emulsifier.

The amount of the core polymerisate used is generally for about 30 wt. % to about 99.5 wt. % and preferably from about 60 wt. % to about 99 wt. % based on the sum of core polymerisate and monomer to be polymerised or monomers to be polymerised.

The chain-propagating agent of the aminophenyldisulphide or aminophenylmercaptan type is especially o,o'-dithiobisaniline, p,p'-dithiobisaniline, 2-mercaptoaniline, 3-mercaptoaniline or 4-mercaptoaniline. This agent is in general used in solution in the monomer(s) in an amount of from about 0.1 wt. % to about 10 wt. %, preferably from about 0.5 wt. % to about 5 wt. % based on the monomer(s).

The initiators generally utilized for the polymerisation of the monomer(s) of the outer layer are diazo initiators, azonitriles such as azo-bis-isobutyronitrile or sulphonated azonitriles as are described in French Pat. No. 1 233 582. Of these there can be mentioned azobis-(isobutyronitrile sodium sulphonate), azobis-(α-methylbutyronitrile sodium sulphonate), azobis-(α-methyl-β-ethoxycarbonylbutyronitrile sodium sulphonate); carboxylated azonitriles such as 4,4'-azobis-(4-cyanopentanoic acid) and their salts, azobis-alkylamidinium salts such as α,α'-azobis-isobutyramidinium chloride and azobis-N,N'-dimethyleneisobutyramidinium chloride.

The initiator, which may be used is preferably used in an amount of from about 0.01 wt. % to about 3 wt. %, preferably from about 0.1 wt. % to about 2 wt. %, based on the monomer(s), is used all together or in part before the polymerisation, whereby the other part is added to the reaction medium in the course of the polymerisation in successive fractions or continuously, especially when the life of the initiator is short at the polymerisation temperature. The initiator can also be added continuously to the reaction mixture all together in the course of the polymerisation.

The emulsifier, which is optionally used, is chosen from the anion-active and/or non-ionic emulsifiers of the kind mentioned earlier in connection with the manufacture of the core polymerisate. The emulsifier can be similar or different to the emulsifier used for the manufacture of the core polymerisate. It is used in an amount up to 10 wt. % based on the monomer(s) and its introduction can be carried out, depending on the desired average diameter of the latex particles, either all together before the polymerisation or in part before the polymerisation, whereby the remaining part is added in the course of the polymerisation in the successive fractions or continuously, or it can be carried out all together in the course of the polymerisation in successive fractions or continuously.

The amount of water which is used in the polymerisation of the outer layer must be such that the concentration of core polymerisate and monomer to be polymerised or monomer(s) to be polymerised does not exceed about 60 wt.%, preferably about 45 wt.%.

The temperature at which the polymerisation is carried out is a function of the chosen initiator and preferably is from about 5° C. to about 100° C., preferably from about 40° C. to about 90° C.

The lattices obtained have polymerisation particles whose diameter lies from about 0.03 μm to about 5 μm, preferably from about 0.05 μm to about 1 μm. Since the amount of the outer layer is not very large, it does not modify the size of the particles of the core polymerisate in an appreciable manner. The particles can be calibrated or not, but for certain uses it is preferred on grounds of reproducibility that they are calibrated, i.e. that they have a narrow particle size distribution.

The lattices are mechanical and are stable upon storage as well as towards electrolytes, i.e. they do not flock out when there are added to them mineral salts such as, for example, the chlorides, nitrates, borates and phosphates of sodium, calcium, magnesium and potassium.

The particles are formed from polymerisates and have a surface with carboxyl and/or sulphonate functions as well as groups of the formula

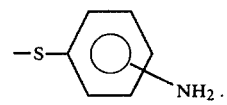

Although the outer layer of the core polymerisate is polymerised, the carboxyl and/or sulphonate functions remain accessible, as can be shown by conductometric titration, and the groups of the formula

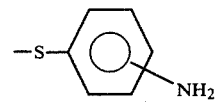

are available for further reactions.

The immunologically active materials (antigen or antibody) can be bound physically and/or chemically to the latex polymers used in accordance with the invention.

In one embodiment, the reagent provided by the present invention is manufactured by forming an azo bond between the latex and the immunologically active material. For this purpose, the primary aromatic amino groups of the latex are converted into a diazonium salt by treatment of the latex in aqueous acidic solution with a nitrate.

An inorganic acid such as hydrochloric acid, sulphuric acid or perchloric acid can be used, for example, as the acid. Sodium nitrite or potassium nitrite is preferably used as the nitrite. The treatment is preferably carried out at 0°–5° C. because of the instability of the diazonium salt.

The immunologically active material is subsequently reacted with the diazotised carrier in aqueous medium, preferably at a temperature between 0° C. and room temperature.

In a further embodiment of the process provided by the present invention, the immunologically active material can be bound to the latex with the aid of a polyfunctional compound via an intermediate stage.

Suitable polyfunctional compounds are those which react with the aromatic amino groups of the latex polymers or which enter into a substitution reaction on the aromatic ring of the latex polymers and simultaneously react with functional groups of the immunologically active materials (e.g. amino, mercapto, carboxyl and hydroxyl groups) or enter into a substitution reaction on the aromatic ring of the immunologically active materials.

Examples of such polyfunctional compounds are compounds containing azo, isocyano, isothiocyano or aldehyde groups such as, for example, bis-diazobenzidine, bis-diazobenzidine-disulphonic acid, bis-diazo-p-phenyldiamine, phenyldiisocyanate, toluenediisocyanate and glutardialdehyde.

When the reaction is carried out in the presence of a bifunctional compound, the immunologically active material is reacted with the carrier in aqueous medium, preferably at room temperature (20° C. to 25° C.). The temperature can, however, also lie between 0° C. and 40° C.

The amount of bifunctional compound used depends on the number of amino groups on the latex. Preferably, there is used a ten-fold to hundred-fold molar excess of the bifunctional compound based on the number of the amino groups on the latex used.

In both embodiments for the manufacture of the reagent provided by the present invention the pH value of the reaction medium is important. The pH value must be such that a protein reaction partner is not denatured. As a rule, the pH value lies between 5 and 9. This pH value is maintained using suitable customary buffer systems such as phosphate buffer and the like.

The end product is a water-insoluble material, which is suspended in an aqueous buffer solution of pH value 5.0 to 9, whereby the pH value of the solution is dependant on the individually used system and on the requirements on the stability of the immunologically active materials. The specific weight of the product corresponds to about that of water (0.97–1.02), whereby a stable suspension of the product is achieved. The products can be isolated, for example by centrifugation, in the form of a white or yellowish precipiatate.

The amount of immunologically active material which is bound to the immunologically inert latex polymer-carrier 0.01 wt. % to 15.0 wt. %. However, each individual immunologically active material is used in an amount which is most convenient in a particular diagnostic test. On this basis, each immunologically active material is combined with the carrier in a ratio which best corresponds to the respective specific requirements. The present invention therefore includes the use of such an amount of immunologically active material in combination with an immunologically inert latex polymer-carrier which is suitable to yield a reagent which is useful for such diagnostic purpose.

After its manufacture, the product can be used in specific diagnostic tests which are based on immunological principles.

In accordance with the present invention, the determination of the immunologically active substances can be carried out not only in a direct test method but also in an indirect (inhibition) test method.

In the direct test method for the determination of an immunologically active substance, the analytical sample and the carrier particles sensitised with the corresponding immunological reaction partner are mixed and the occurrence of an agglutination is observed. The test is positive when an agglutination is established.

In the case of the indirect (inhibition) test method for the determination of an immunologically active substance, the analytical sample is mixed with a determined amount of the corresponding immunological reaction partner (e.g. antiserum) and latex particles which are sensitised with the immunologically active substance and the occurrence of an agglutination is observed. The test is positive when no agglutination is established.

The reagents used in such immunological test methods can advantageously be packed for commercial purposes in a diagnostic test kit.

In the case of a direct test, the reagent kit for the determination of an immunologically active substance contains in a container an aqueous suspension of latex particles sensitized with the corresponding immunological reaction partner.

In the case of an indirect test, the reagent kit for the determination of an immunologically active substance contains in a first container a solution of the corresponding immunological reaction partner (e.g. antiserum) and in a second container an aqueous suspension of latex particles sensitised with the immunologically active material.

In both cases, the aqueous suspension of the immunologically active materials bound to latex or the immunological reaction partners bound to latex can be present in any concentration. However, a concentration of from about 0.5 wt. % to about 5 wt. % is preferred.

The term alkali includes all alkali metals such as lithium, sodium, potassium, etc.. The term alkyl designates alkyl groups containing 1 to 10 carbon atoms. The term carboxylic and dicarboxylic acids include aliphatic carboxyl and dicarboxylic acids containing 2 to 10 carbon atoms. The term fatty acid includes aliphatic acids containing from 10 to 20 carbon atoms.

The following examples illustrate the present invention:

EXAMPLE 1

A latex of core polymerisate is manufactured in a 25 liter autoclave, there being used:
4800 g of deionised water,
50 g of potassium persulphate,
50 g of sodium pyrophosphate,
10 g of sodium lauryl sulphate,
50 g of sodium methallyl sulphonate,
100 g of acrylic acid,
100 g of itaconic acid,
2135 g of styrene and
2865 g of butadiene.

The polymerisation is carried out at 75° C. under a nitrogen atmosphere, the monomers being introduced continuously over a period of 7 hours and the reaction being continued for 8 hours.

After cooling down, there is obtained a latex of pH 2.5, whose concentration of polymerisate particles amounts to 51 wt.%.

By electron microscopy it is established that the particles have an average diameter of 0.145 μm and 90% of the particles have a diameter between 0.14 and 0.15 μm.

The composition of the polymerisate is essentially similar to that of the monomers used. The particles carry on their surface carboxyl and sulphonate functions which are determined by conductometric titration.

406 g of the foregoing latex and 1541 g of deionised water are introduced into a reactor. The mixture is heated to 70° C. while stirring and this temperature is maintained during the entire duration of the reaction.

As soon as the mixture has attained 70° C., it is held under a nitrogen atmosphere and there are simultaneously added thereto in 3 hours with constant velocity 1.25 g of sodium dihexylsulphosuccinate in 150 g of water, 0.20 g of α,α'-azobis-isobutyramidinium chloride in 210 g of water and 18 g of styrene containing 0.45 g of p,p'-dithiobisaniline.

The polymerisation is then continued for 5 hours. The mixture is thereafter cooled down.

Properties of the resulting latex:
pH: 3.1;
concentration of polymerisation particles: 9.3 wt.%;
electrolyte stability: 5;
average diameter of the particles: 0.15 μm, 90% having a diameter between 0.145 μm and 0.155 μm.

The particles carry on their surface carboxyl and sulphonate functions, which are confirmed by conductometric titration, and groups of the formula

1 ml of the 10% latex obtained is added to 20 ml of water and the mixture is centrifuged for 1.5 hours at 35,000 g. The supernatant is decanted off, the residue is taken up in 20 ml of water and again centrifuged for 1.5 hours at 35,000 g. This operation is repeated twice and the thus-obtained latex is denoted in the following examples as "washed latex".

5 mg of human immunoglobulin G (Cohn fraction II) is denatured by heating to 60° C. for 3 hours in 1 ml of 0.1-M glycine/hydrochloric acid buffer pH 4.

1 ml of washed latex is added to 5 ml of 0.05-M hydrochloric acid and the mixture is cooled down to 0° C. To this mixture is added 0.1 ml of a 0.01-M sodium nitrite solution and the resulting mixture is stirred at 0° C. for 15 minutes. The diazotised latex is centrifuged at 5° C. for 1.5 hours at 35,000 g and the supernatant is decanted off. The residue is taken up in 5 ml of ice-cold 0.1-M glycine/hydrochloric acid buffer pH 4.0 and added to 1 ml of 0.5% denatured human immunoglobulin G in the same buffer, stirred for 1 hour in an ice-bath and subsequently left to stand at 10° C. overnight. The latex is centrifuged for 1.5 hours at 35,000 g, the supernatant is decanted off and the residue is washed twice with in each case 25 ml of 0.1-M glycine/sodium hydroxide buffer pH 8.2 by centrifugation and suspension of the residue. Sufficient buffer is now added to the latex to give a solution containing 30 mg/ml.

Agglutination test:

For the test tube agglutination test the following buffer is used: 7.5 g of glycine, 6.0 g of calcium chloride, 3 g of bovine albumin and 1 g of sodium azide dissolved in 1 liter of water. The pH value is adjusted to 8.2 with sodium hydroxide. For the detection of the rheumatoid factors in serum, 20 μl of latex is diluted with 3 ml of buffer in a small test tube and 25 μl of the serum to be investigated are added. After intermixing, the test tubes are held at 37° C. during 2 hours in a heat-block. A positive serum agglutinates under these conditions while a negative control system shows no agglutination.

EXAMPLE 2

1 ml of washed latex is manufactured and diazotised as described in Example 1. To the diazotised latex residue are added 5 ml of ice-cold 0.1-M glycine/sodium hydroxide buffer pH 6.0, 5 ml of goat anti-human albumin immunoglobulin G dissolved in 1 ml of foregoing buffer are added and, after stirring for 1 hour at 10° C., the mixture is left to stand overnight. The latex is centrifuged at 35,000 g for 1.5 hours, the supernatant is discarded and the sediment is washed twice with in each case 25 ml of 0.1-M glycine/sodium hydroxide pH 8.2. After washing, the latex is mixed with sufficient buffer to give a 3% solution.

Agglutination test:

For the test tube agglutination test the following buffer is used: 7.5 g of glycine, 6.0 g of calcium chloride, 3 g of bovine albumin and 1.0 g of sodium azide dissolved in 1 liter of water. The pH is adjusted to 6.0 with hydrochloric acid. A concentration series of human albumin in 3 ml of buffer is set up in small test tubes, in each case 2 μl of latex are added and, after intermixing, held for 2 hours at 37° C. in a heat-block.

| 20 | 10 | 1 | 0.1 | 0.05 | 0.01 | 0 | μg human albumin/ml buffer |
|---|---|---|---|---|---|---|---|
| + | + | + | + | + | − | − | |

+ = agglutinates in 2 hours
− = does not agglutinate in 2 hours

From this Table it is evident that 0.05 μg of human albumin/ml can be determined with the latex reagent of this Example.

EXAMPLE 3

1 ml of the washed latex of Example 1 is added to 5 ml of 0.1-M phosphate buffer pH 5.0, 5 mg of sheep anti-human IgG immunoglobulin G in 1 ml of buffer are added and the mixture is stirred well. Subsequently, 0.1 ml of a 0.01-M p-phenyldiisothiocyanate solution in dimethylformamide is added, the mixture is stirred for 1 hour and left to stand at room temperature overnight. The latex is centrifuged for 1.5 hours at 35,000 g, the supernatant is discarded and the residue is washed twice with in each case 25 ml of 0.1-M glycine/sodium hydroxide buffer pH 8.2. For the agglutination test the latex is used in a concentration of 30 mg/ml.

Agglutination test:

For the test tube agglutination test there is used a 0.1-M phosphate buffer pH 6.0 with 0.1% bovine albumin. A concentration series of human IgG in 3 ml of buffer is prepared. To each test tube are added 20 μl of latex reagent, the test tube contents are intermixed and incubated for 2 hours at 37° C. in a heat-block.

| 100 | 10 | 1 | 0,1 | 0.05 | 0 | μg human IgG/ml buffer |
|---|---|---|---|---|---|---|
| + | + | + | + | − | − | |

+ = agglutinates in 2 hours
− = does not agglutinate in 2 hours

The Table shows that 0.1 μg/ml of human IgG can be determined with the latex reagent of this Example.

EXAMPLE 4

36.8 mg of benzidine are dissolved in 0.5 ml of 2-N sodium chloride and diluted with 7.5 ml of water. The mixture is cooled in an ice-bath and added dropwise while stirring to 27.2 mg of sodium nitrite in 2 ml of water. The thus-obtained bisdiazotised benzidine can be stored at −20° C. for weeks.

1 ml of the washed latex of Example 1 is taken up in 5 ml of 0.1-M phosphate buffer pH 7.0 and 5 mg of human immunoglobulin G in 1 ml of the foregoing buffer are added. The suspension is cooled down to 0° C. and, while stirring, 0.01 ml of a 0.02-M bisdiazotised benzidine solution is added. The mixture is then left to stand at 10° C. overnight. The latex is centrifuged at 30,000 g for 1.5 hours, the supernatant is discarded and the sediment is washed twice with in each case 25 ml of 0.1-M glycine/sodium hydroxide pH 8.2. After washing, the latex is mixed with sufficient buffer to give a 3% solution.

Agglutination test:

For the determination of IgG in an inhibition test, a 0.1-M phosphate buffer pH 6.0 is used. In each case 3 ml of a 1/500 diluted sheep anti-human IgG serum and increasing amounts of human IgG are added to small test tubes. After incubation for 15 minutes at 37° C., there is added to each test tube 20 μl of latex reagent and the mixture is incubated for 3 hours at 37° C.

| 0.01 | 0.01 | 0.10 | 0.50 | 1.0 | 5.0 | μg human IgG/3 ml |
|------|------|------|------|-----|-----|-------------------|
| +    | +    | +    | +    | −   | −   |                   |

+ = agglutinates in 3 hours
− = does not agglutinate in 3 hours 0.16 μg of human IgG/ml can be determined with the latex reagent of this Example.

I claim:

1. A reagent for an immunological determination comprising a water insoluble reagent in the form of discrete latex particles, said reagent having a specific weight corresponding to about that of water, said latex particles being formed from vinyl polymerizates and having free terminal functional groups of the formula

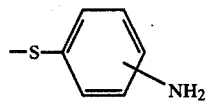

through which is bound an immunologically active material, wherein said latex particles contain a core and an outer layer, said core containing polymerizates formed from vinyl or dienes monomers or mixtures thereof, with said polymerizates in said core carrying a functional group selected from the group consisting of carboxyl, sulfonate or mixtures thereof and said outer layer containing vinyl polymerizates carrying said terminal funtional groups.

2. The reagent of claim 1, wherein said latex particles have an average diameter of from about 0.03 μm to about 5 μm.

3. The reagent of claim 2, wherein the vinyl polymerizates are homopolymerizates of monomers selected from the group consisting of vinyl chloride, vinylidene chloride, vinyl acetate, acryl derivatives, styrene and styrene derivatives, copolymerizates of said monomers with one another or copolymerizates of said monomers with modified vinyl comonomers which constitute up to 5 wt.% of the copolymerizate.

4. The reagent of claim 2 wherein the diene polymerizates are homopolymerizates of a diene monomer selected from the group consisting of butadiene and its derivatives or copolymerizates of said diene monomers with one another, with vinyl monomers, with modified vinyl comonomers constituting up to 5 wt.% of the copolymerizate, or with mixtures thereof.

5. The reagent of claim 3, wherein the vinyl polymerizates which form the outer layer are homopolymerizates of olefin monomers selected from the group consisting of styrene, styrene derivatives, alkyl acrylates, alkyl methacrylates, acrylonitrile and methacrylonitrile, or copolymerizates of said olefin monomers, or copolymerizates of said olefin monomers with modified acting vinyl comonomers wherein the said vinyl comonomers constitute up to 5 wt.% of the copolymerizates.

6. A reagent according to any one of claim 2, wherein the core polymerizate comprises from about 30 wt.% to about 99.5 wt.% of the latex particle and the polymerizate of the outer layer constitutes from about 70 wt.% to about 0.5 wt.% of the latex particle.

7. The reagent of claim 1, wherein the amount of immunologically active material is from about 0.01 wt.% to about 15.0 wt.% based upon the latex.

8. The reagent of claim 7, wherein the immunologically active material is bound covalently to said terminal functional groups on the discrete latex particles.

9. The reagent of claim 1, wherein the immunologically active material is human immunoglobulin G.

10. The reagent of claim 1, wherein the immunologically active material is goat anti-human albumin immunoglobulin G.

11. The reagent of claim 1, wherein the immunologically active material is sheep anti-human IgG immunoglobulin G.

12. The reagent of claim 1, wherein the immunologically active material is bound to the latex through the diazotization of the terminal functional group.

13. The reagent of claim 1 wherein the immunologically active material is bound to the latex by means of a bifunctional compound which reacts with the free terminal functional group of the latex and the immunologically active material.

14. A process for preparing a reagent for immunological determination comprising reacting discrete latex particles formed from vinyl polymerizates and having a specific weight corresponding to about that of water and having free terminal functional group of the formula:

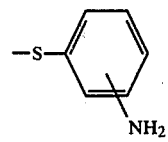

with an immunologically active material, wherein said latex particles contain a core and an outer layer, said core formed by polymerization of vinyl, or diene monomers or mixtures thereof with said polymerizates in said core carrying a functional group selected from group consisting of carboxyl, sulfonate or mixtures thereof and said outer layer formed from vinyl polymerizates carrying said terminal functional group.

15. The process of claim 14 wherein the latex particles have a diameter of about 0.03 μm to about 5 μm.

16. The process of claim 15 wherein the immunologically active material is bound to the latex through the diazotization of said function terminal group.

17. The process of claim 16 wherein said immunologically active material is denatured immunoglobulin G.

18. The process of claim 15 wherein the immunologically active material is goat anti-human albumin immonoblogulin G.

19. The process of claim 15 wherein the immunologically active material is bound to said terminal functional groups of said latex through a bifunctional compound.

20. The process of claim 19 wherein said bifunction compound is p-phenyl diisothiocyanate or bis-diazobenzidine.

* * * * *